United States Patent
Ma et al.

(10) Patent No.: US 10,426,605 B2
(45) Date of Patent: Oct. 1, 2019

(54) DEVICE AND METHOD FOR MITRAL VALVE REGURGITATION TREATMENT

(71) Applicant: Sino Medical Sciences Technology, Inc., Tianjin (CN)

(72) Inventors: Jianlu Ma, Irvine, CA (US); Yong Huo, Beijing (CN); Tianzhu Li, Foothill Ranch, CA (US); Jinhong Zhao, Foothill Ranch, CA (US); Jianxiang Ma, Foothill Ranch, CA (US); Lei Meng, Foothill Ranch, CA (US)

(73) Assignee: Sino Medical Sciences Technology, Inc., Tianjin (CN)

(*) Notice: Subject to any disclaimer, the term of this patent is extended or adjusted under 35 U.S.C. 154(b) by 0 days.

(21) Appl. No.: 15/808,822

(22) Filed: Nov. 9, 2017

(65) Prior Publication Data

US 2018/0071084 A1    Mar. 15, 2018

Related U.S. Application Data

(63) Continuation of application No. 15/025,008, filed as application No. PCT/US2014/059076 on Oct. 3, (Continued)

(51) Int. Cl.
    *A61F 2/24* (2006.01)
(52) U.S. Cl.
    CPC ............ *A61F 2/24* (2013.01); *A61F 2/2412* (2013.01); *A61F 2/2418* (2013.01); (Continued)
(58) Field of Classification Search
    None
    See application file for complete search history.

(56) References Cited

U.S. PATENT DOCUMENTS 5,411,552 A    5/1995  Andersen et al.
5,413,599 A    5/1995  Imachi et al.
(Continued)

FOREIGN PATENT DOCUMENTS

CA    2874208 A1    11/2013
CA    2903600 A1    9/2014
(Continued)

OTHER PUBLICATIONS

Supplementary European Search Report and Written Opinion, dated May 30, 2017, in a counterpart EP application, No. EP 14853635.2.
(Continued)

*Primary Examiner* — Suba Ganesan
(74) *Attorney, Agent, or Firm* — Chen Yoshimura LLP

(57) ABSTRACT

A mitral valve replacement device is adapted to be deployed at a mitral valve position in a human heart. The device has an atrial flange defining an atrial end of the device, a ventricular portion defining a ventricular end of the device, the ventricular portion having a height ranging between 2 mm to 15 mm, and an annulus support that is positioned between the atrial flange and the ventricular portion. The annulus support includes a ring of anchors extending radially therefrom, with an annular clipping space defined between the atrial flange and the ring of anchors. A plurality of leaflet holders positioned at the atrial end of the atrial flange, and a plurality of valve leaflets secured to the leaflet holders, and positioned inside the atrial flange at a location above the native annulus.

7 Claims, 15 Drawing Sheets

Related U.S. Application Data 2014, now Pat. No. 9,839,511, which is a continuation-in-part of application No. 14/279,511, filed on May 16, 2014, now Pat. No. 9,393,111.

(60) Provisional application No. 61/927,490, filed on Jan. 15, 2014, provisional application No. 62/024,097, filed on Jul. 14, 2014, provisional application No. 61/887,343, filed on Oct. 5, 2013.

(52) U.S. Cl.
CPC ..... *A61F 2/2409* (2013.01); *A61F 2210/0014* (2013.01); *A61F 2220/005* (2013.01); *A61F 2220/0008* (2013.01); *A61F 2230/005* (2013.01); *A61F 2230/0052* (2013.01); *A61F 2250/0039* (2013.01)

(56) References Cited

U.S. PATENT DOCUMENTS

| | | | |
|---|---|---|---|
| 5,824,064 A | 10/1998 | Taheri | |
| 5,957,949 A | 9/1999 | Leonhardt | |
| 6,425,916 B1 | 7/2002 | Garrison et al. | |
| 6,458,153 B1 | 10/2002 | Bailey et al. | |
| 6,494,909 B2 | 12/2002 | Greenhalgh | |
| 6,572,652 B2 | 6/2003 | Shaknovich | |
| 6,582,462 B1 | 6/2003 | Andersen et al. | |
| 6,652,578 B2 | 11/2003 | Bailey et al. | |
| 7,329,278 B2 | 2/2008 | Seguin et al. | |
| 7,452,371 B2 | 11/2008 | Pavcnik et al. | |
| 7,510,574 B2 | 3/2009 | Le et al. | |
| 7,618,446 B2 | 11/2009 | Andersen et al. | |
| 7,748,389 B2 | 7/2010 | Salahieh et al. | |
| 7,947,075 B2 | 5/2011 | Goetz et al. | |
| 8,070,802 B2 | 12/2011 | Lamphere et al. | |
| 8,252,051 B2 | 8/2012 | Chau et al. | |
| 8,403,983 B2 | 3/2013 | Quadri et al. | |
| 8,449,599 B2 | 5/2013 | Chau et al. | |
| 8,506,620 B2 | 8/2013 | Ryan | |
| 8,613,763 B2 | 12/2013 | Pavcnik et al. | |
| 2002/0032481 A1 | 3/2002 | Gabbay | |
| 2002/0123802 A1 | 9/2002 | Snyders | |
| 2002/0138138 A1 | 9/2002 | Yang | |
| 2002/0151970 A1 | 10/2002 | Garrison et al. | |
| 2003/0023300 A1 | 1/2003 | Bailey | |
| 2003/0023303 A1 | 1/2003 | Palmaz | |
| 2003/0149477 A1 | 8/2003 | Gabbay | |
| 2003/0191527 A1 | 10/2003 | Shaknovich | |
| 2005/0137686 A1 | 6/2005 | Salaheih et al. | |
| 2005/0182486 A1 | 8/2005 | Gabbay | |
| 2005/0203616 A1 | 9/2005 | Cribier | |
| 2006/0142848 A1 | 6/2006 | Gabbay | |
| 2006/0149360 A1 | 7/2006 | Schwammenthal et al. | |
| 2007/0078510 A1 | 7/2007 | Ryan | |
| 2007/0168024 A1 | 7/2007 | Khairkhahan | |
| 2007/0198097 A1 | 8/2007 | Zegdi | |
| 2007/0270943 A1 | 11/2007 | Solem et al. | |
| 2008/0004688 A1 | 1/2008 | Spenser et al. | |
| 2009/0234446 A1 | 9/2009 | Berreklouw | |
| 2010/0249923 A1 | 9/2010 | Alkhatib et al. | |
| 2011/0098800 A1 | 4/2011 | Braido et al. | |
| 2011/0106246 A1 | 5/2011 | Malewicz et al. | |
| 2011/0112632 A1 | 5/2011 | Chau et al. | |
| 2011/0208298 A1 | 8/2011 | Tuval et al. | |
| 2011/0319988 A1 | 12/2011 | Schankereli et al. | |
| 2011/0319989 A1 | 12/2011 | Lane et al. | |
| 2012/0016464 A1 | 1/2012 | Seguin | |
| 2012/0022639 A1 | 1/2012 | Hacohen et al. | |
| 2012/0046741 A1 | 2/2012 | Tuval et al. | |
| 2012/0078353 A1 | 3/2012 | Quadri et al. | |
| 2012/0095551 A1 | 4/2012 | Navia et al. | |
| 2012/0101572 A1 | 4/2012 | Kovalsky et al. | |
| 2012/0179244 A1 | 7/2012 | Schankereli et al. | |
| 2012/0191182 A1 | 7/2012 | Hauser et al. | |
| 2012/0323313 A1 | 12/2012 | Seguin | |
| 2012/0323316 A1 | 12/2012 | Chau et al. | |
| 2013/0090728 A1 | 4/2013 | Solem | |
| 2013/0131793 A1 | 5/2013 | Quadri et al. | |
| 2013/0138207 A1 | 5/2013 | Quardi et al. | |
| 2013/0144380 A1 | 6/2013 | Quadri et al. | |
| 2013/0172992 A1 | 7/2013 | Gross et al. | |
| 2013/0184811 A1 | 7/2013 | Rowe et al. | |
| 2013/0190861 A1* | 7/2013 | Chau ............ A61F 2/2418 623/2.18 |
| 2013/0211508 A1 | 8/2013 | Lane et al. | |
| 2014/0046434 A1 | 2/2014 | Rolando et al. | |
| 2014/0214159 A1 | 7/2014 | Vidlund et al. | |
| 2014/0257467 A1 | 9/2014 | Lane et al. | |
| 2014/0277390 A1* | 9/2014 | Ratz ............ A61F 2/2418 623/1.26 |
| 2015/0142103 A1 | 5/2015 | Vidlund | |
| 2015/0257878 A1 | 9/2015 | Lane et al. | |
| 2016/0030171 A1* | 2/2016 | Quijano ............ A61F 2/243 623/1.12 |

FOREIGN PATENT DOCUMENTS

| | | |
|---|---|---|
| EP | 1264582 A2 | 12/2002 |
| EP | 2047824 A1 | 4/2009 |
| WO | 2003/003943 A2 | 1/2003 |
| WO | 2003/030776 A1 | 4/2003 |
| WO | 2003/047468 A1 | 6/2003 |
| WO | 2004/019825 A1 | 3/2004 |
| WO | 2009/053497 A1 | 4/2009 |
| WO | 2009/134701 A2 | 11/2009 |
| WO | 2013/059747 A1 | 4/2013 |
| WO | 2013/075215 A1 | 5/2013 |

OTHER PUBLICATIONS

International Search Report in the parent PCT application No. PCT/US2014/059076, dated Feb. 6, 2015.

IPRP in the parent PCT application No. PCT/US2014/059076, dated Apr. 5, 2016.

Japanese Office Action, dated Jul. 24, 2018 in a counterpart Japanese patent application, No. JP 2016-546888.

Canadian Office Action, dated Nov. 9, 2018, in a counterpart Canadian patent application, No. 2,922,123.

* cited by examiner

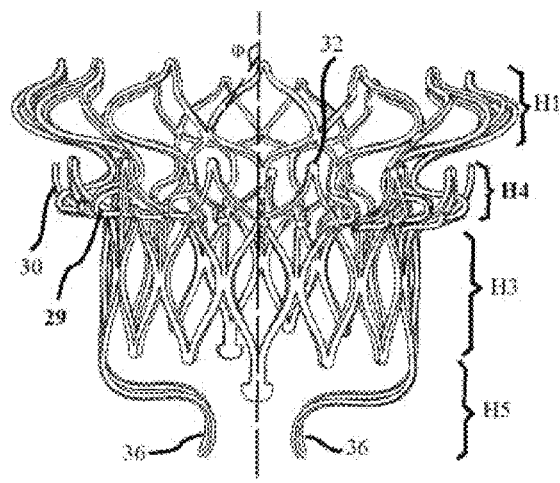
FIG. 5A
FIG. 5B
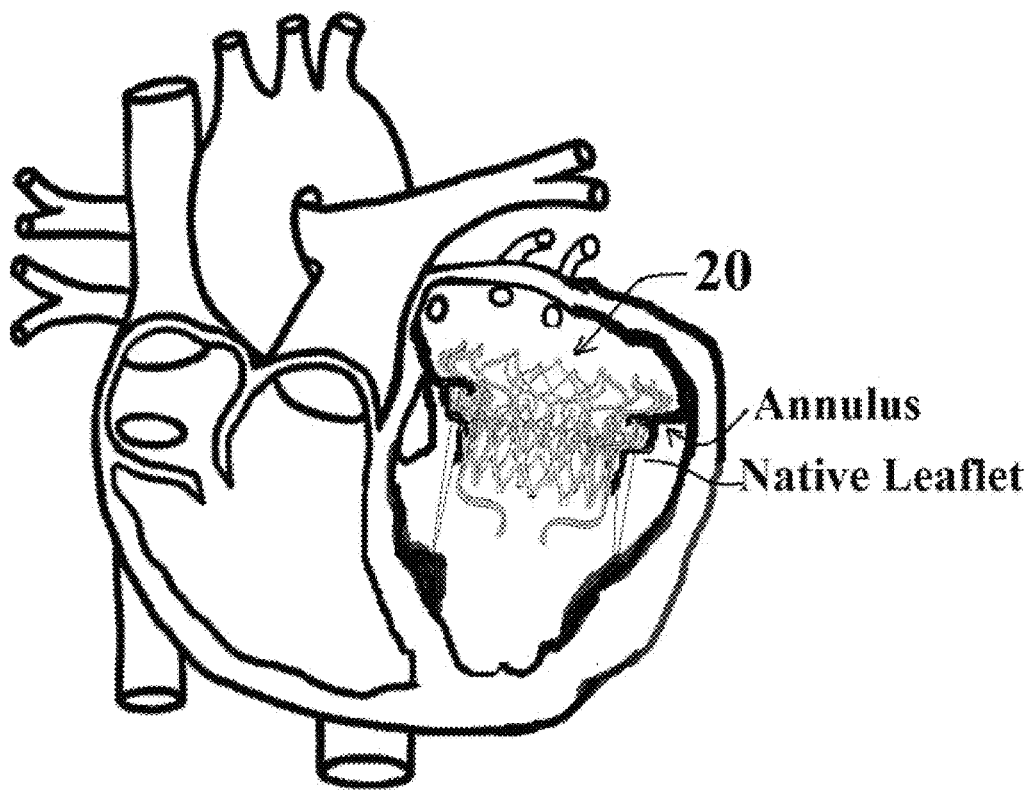

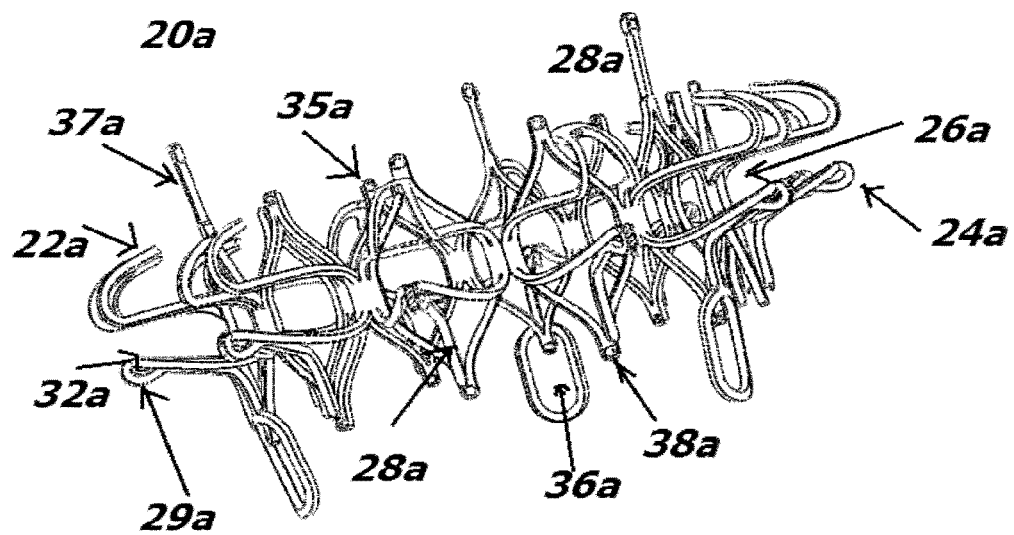
Fig. 16
Fig. 18
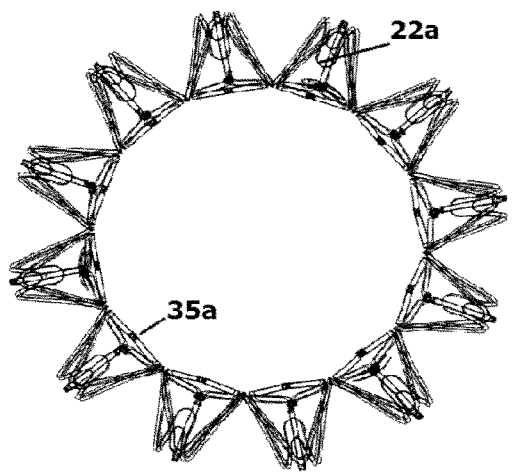
Fig. 17
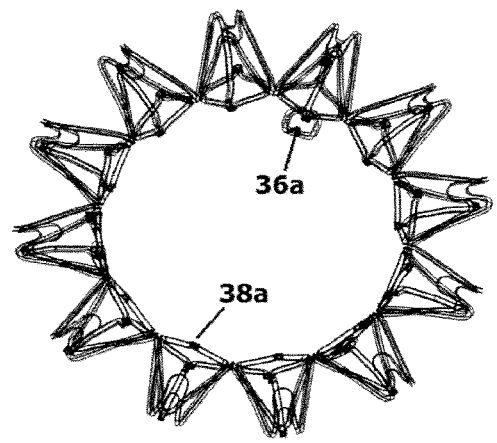

DEVICE AND METHOD FOR MITRAL VALVE REGURGITATION TREATMENT

RELATED CASES

This application is related to Provisional Application No. 62/024,097, filed Jul. 14, 2014, Provisional Application No. 61/927,490, filed Jan. 15, 2014, and Provisional Application No. 61/887,343, filed Oct. 5, 2013. This application is a continuation-in-part of U.S. application Ser. No. 14/279,511, filed May 16, 2014, whose entire disclosure is incorporated by this reference as though set forth fully herein.

BACKGROUND OF THE INVENTION

1. Field of the Invention

The present invention generally relates to medical devices and methods useful for human mitral valve function repair and/or reconstruction. In particular, the present invention relates to a medical device that can be used to treat mitral valve regurgitation by replacing the function of native heart valves.

2. Description of the Prior Art

The human heart has four chambers and four valves. The heart valves control the direction of blood flow. Fully-functional heart valves ensure proper blood circulation is maintained during cardiac cycle. Heart valve regurgitation, or leakage, occurs when the leaflets of the heart valve fail to come fully into contact (coapt) due to disease, such as congenital, torn chordae tendineae, lengthened chordae tendineae, enlarged left ventricle, damaged papillary muscles, damaged valve structures by infections, degenerative processes, calcification of the leaflets, stretching of the annulus, increased distance between the papillary muscles, etc. Regardless of the cause, the regurgitation interferes with heart function since it allows blood to flow back through the valve in the wrong direction. Depending on the degree of regurgitation, this backflow can become a self-destructive influence on not only the function, but also on the cardiac geometry. Alternatively, abnormal cardiac geometry can also be a cause of regurgitation, and the two processes may "cooperate" to accelerate abnormal cardiac function. The direct consequence of the heart regurgitation is the reduction of forward cardiac output. Depending on the severity of the leakage, the effectiveness of the heart to pump adequate blood flow into other parts of the body can be compromised.

The mitral valve is a dual-flap (bi-leaflet) valve in the heart that lies between the left atrium (LA) and the left ventricle (LV). During diastole, a normally-functioning mitral valve opens as a result of increased pressure from the left atrium as it fills with blood (preloading). As atrial pressure increases above that of the left ventricle, the mitral valve opens, facilitating the passive flow of blood into the left ventricle. Diastole ends with atrial contraction, which ejects the remainder of blood that is transferred from the left atrium to the left ventricle. The mitral valve closes at the end of atrial contraction to prevent a reversal of blood flow from left ventricle to left atrium. The human mitral valve is typically 4-6 cm$^2$ in opening area. There are two leaflets, the anterior leaflet and posterior leaflet, which cover the opening of the mitral valve. The opening of the mitral valve is surrounded by a fibrous ring called the mitral valve annulus. The two leaflets are attached circumferentially to the mitral valve annulus and can open and close by hinging from the annulus during cardiac cycle. In a normally-functioning mitral valve, the leaflets are connected to the papillary muscles in the left ventricle by chordae tendineae. When the left ventricle contracts, the intraventricular pressure forces the mitral valve to close, while chordae tendineae keep the two leaflets coapting (to prevent two valve leaflets from prolapsing into the left atrium and creating mitral regurgitation) and prevent the valve from opening in the wrong direction (thereby preventing blood from flowing back into the left atrium).

Currently, the standard heart valve regurgitation treatment options include surgical repair/treatment and endovascular clipping. The standard surgical repair or replacement procedure requires open-heart surgery, use of cardio-pulmonary bypass, and stoppage of the heart. Because of the invasive nature of the surgical procedure, risks of death, stroke, bleeding, respiratory problems, renal problems, and other complications are significant enough to exclude many patients from surgical treatment.

In recent years, endovascular clipping techniques have been developed by several device companies. In this approach, an implantable clip made from biocompatible materials is inserted into the heart valve between the two leaflets to clip the middle portion of the two leaflets (mainly A2 and P2 lealfets) together to prevent the prolapse of the leaflets. However, some shortcomings, such as difficulty of positioning, difficulty of removal once implanted incorrectly, recurrence of heart valve regurgitation, the need for multiple clips in one procedure, strict patient selection, etc., have been uncovered in the practical application of endovascular clipping.

In conclusion, there is a great need for developing a novel medical device to treat mitral regurgitation. None of the existing medical devices to date address this need fully. The present invention aims to provide physicians with a device and a method which can avoid a traumatic surgical procedure, and instead provide a medical device that can be implanted through a catheter-based, less invasive procedure for mitral regurgitation treatment.

SUMMARY OF THE DISCLOSURE

It is an object of the present invention to provide a mitral valve replacement device that can be effectively secured to the location of the human mitral valve annulus without piercing of the native tissue.

It is another object of the present invention to provide a method of deploying a mitral valve replacement device at the location of the human mitral valve annulus where the position of the device can be adjusted before final release of the device is completed.

It is yet another object of the present invention to provide a novel leaflet structure that provides more efficient valvular control and flow.

In order to accomplish the objects of the present invention, the present invention provides a mitral valve replacement device adapted to be deployed at a mitral valve position in a human heart. The device has an atrial flange defining an atrial end of the device, a ventricular portion defining a ventricular end of the device, the ventricular portion having a height ranging between 2 mm to 15 mm, and an annulus support that is positioned between the atrial flange and the ventricular portion. The annulus support includes a ring of anchors extending radially therefrom, with an annular clipping space defined between the atrial flange and the ring of anchors. A plurality of leaflet holders positioned at the atrial end of the atrial flange, and a plurality of valve leaflets secured to the leaflet holders, and positioned inside the atrial flange at a location above the native annulus.

BRIEF DESCRIPTION OF THE DRAWINGS

FIG. 5A is another side view of the device of FIG. 1 which is rotated by 90 degrees from the view of FIG. 4.

FIG. 5B illustrates the device of FIG. 1 positioned at the mitral valve annulus of a human heart.

FIG. 16 is a perspective view of a mitral valve device according to a third embodiment of the present invention.

FIG. 17 is a bottom view of the device of FIG. 16.

FIG. 18 is a top view of the device of FIG. 16.

DETAILED DESCRIPTION OF THE PREFERRED EMBODIMENTS

Figure 1:
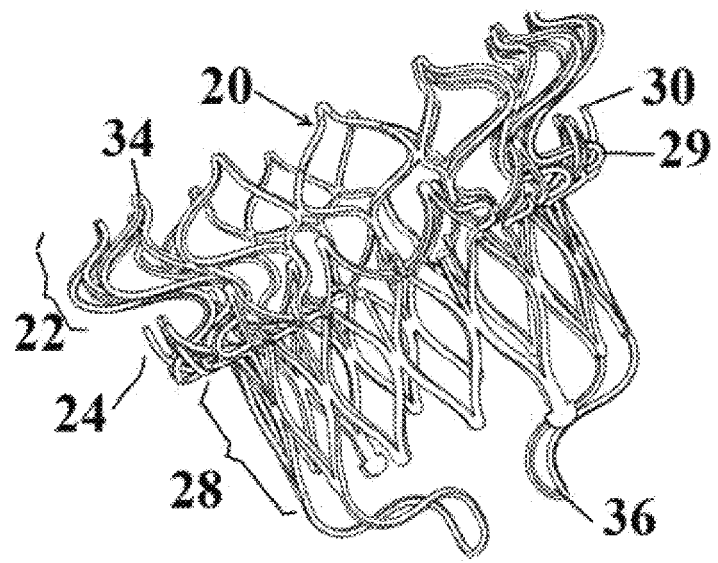
FIG. 1 is a perspective view of a mitral valve device according to a first embodiment of the present invention.
Figure 2:
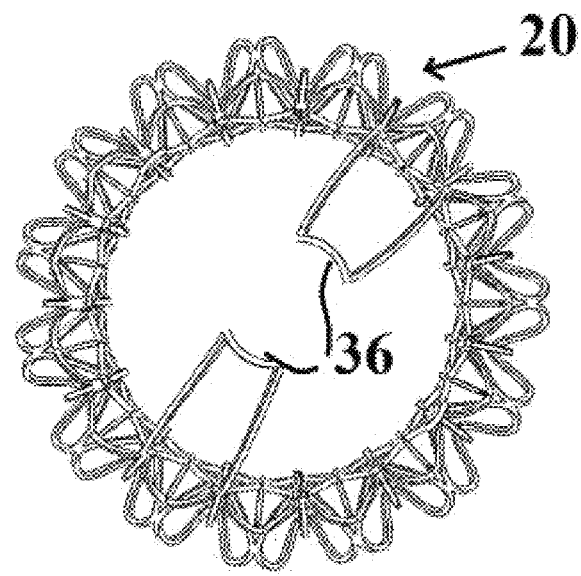
FIG. 2 is a bottom view of the device of FIG. 1.
Figure 3:
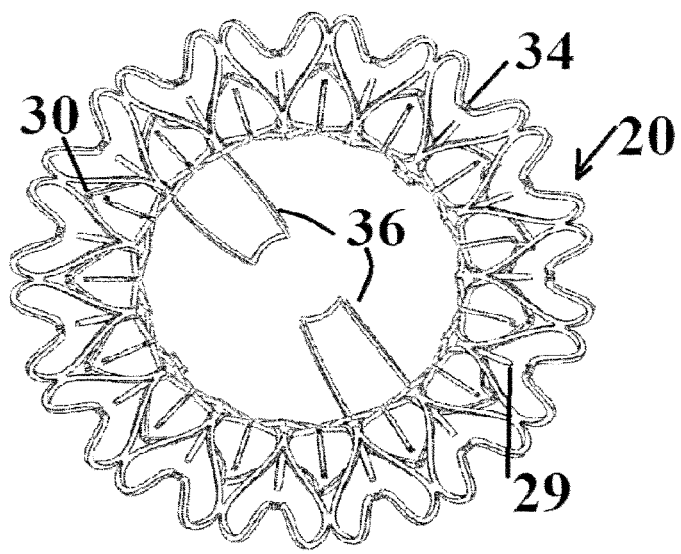
FIG. 3 is a top view of the device of FIG. 1.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The subject technology relates generally to mitral regurgitation treatment devices and to the manner of positioning and anchoring the device in a human heart. This device contains an atrial portion and a ventricular portion. The atrial portion of the device "seats" at the mitral annulus area to create a "seal" to prevent leakage (blood flow back from the left ventricle to the left atrium) from the area surrounding the device. The ventricular portion of the device contains a valve body and anchoring features. The anchoring features can be partially or fully covered by fabric or tissue to create a "seal" to prevent leakage. The valve body contains the tissue leaflet(s) and leaflet supporting structure. During normal cardiac cycle, the valve and leaflet(s) open and close to regulate the direction and volume of the blood flow between the left atrium and the left ventricle. The function of the anchoring features is to maintain the proper position of the device to prevent potential migration during cardiac cycle. The anchoring features provide an anchoring effect by interacting with the native leaflet(s), and/or the annulus, and/or other subvalvular structures. One design of the anchoring feature is to use biocompatible adhesive/glue to form the bond between the device and the native valvular and/or heart structure to maintain the position of the valve prosthesis.

In use, the device will be delivered using a transcatheter approach to the mitral space, and interact with the internal valvular structure and subvalvular structures to restore the function of the mitral valve. In addition, this device can be implanted through surgical or other minimally invasive procedures. The device can be implanted inside of a heart or a lumen in the human vasculature, which serves to improve, replace, and/or reconstruct the function of the native mitral leaflet(s) and mitral valve.

The present invention also covers an anchoring feature (clip design) that utilizes the native leaflet(s), and/or annulus, and/or other sub-annular structures to provide an anchoring effect to maintain the device in position during the cardiac cycle. Once the device is placed in the mitral position, the anchoring feature(s) on the device engage/interacts with the native leaflet(s), and/or annulus, and/or other subvalvular structures to prevent the device from migration during cardiac cycle. The atrial portion of the device can also provide some additional anchoring effect by interacting with the annulus and the atrial portion of the heart above the annulus that is in contact with the atrial portion of the device.

The present invention also provides a novel leaflet design. The leaflet configuration can contain one to six pieces of leaflets, which can be sewn together inside the leaflet supporting structure to form an umbrella shaped profile that can open and close during the cardiac cycle to regulate the flow. During cardiac systole (heart contraction), the umbrella-shaped leaflets can open to a larger profile and to close the mitral valve, so that there is no blood flow back to the left atrium from the left ventricle. During cardiac diastole (heart relaxation), the umbrella-shaped leaflets can close to a smaller profile and to open the mitral valve, so that blood can flow from the left atrium to the left ventricle. The advantages of this novel valve leaflet design include: (i) no axial contraction/squeezing to the leaflet supporting structure by the leaflet(s) during the cardiac cycle, so as to improve the fatigue resistance of the supporting structure; (ii) better leaflet(s) coaptation, where the coaptation is between the leaflet(s) and the skirt(s) on the supporting structure, which minimizes the potential for central leakage, and (iii) there is no "free edge" at the central portion of the leaflet(s). There is no coaptation between/among the leaflet(s). This feature is important because any deformation or distortion of the valve supporting structure would result in minimal central leakage.

The mitral valve replacement device of the present invention can be compacted into a low profile and loaded onto a delivery system, and then delivered to the target location by a non-invasive medical procedure, such as through the use of a delivery catheter through transapical, or transfemoral, or transseptal procedures. The mitral valve replacement device can be released from the delivery system once it reaches the target implant site, and can expand to its normal (expanded) profile either by inflation of a balloon (for a balloon expandable supporting structure) or by elastic energy stored in the device (for a device with a self-expandable supporting structure).

The leaflet(s) in the mitral valve replacement device of the present invention can be made from treated animal tissue/pericardium, from thin wall biocompatible metallic element (such as stainless steel, Co—Cr based alloy, Nitinol, Ta, and Ti etc.), or from biocompatible polymer material (such as polyisoprene, polybutadiene and their co-polymers, neoprene and nitrile rubbers, polyurethane elastomers, silicone rubbers, fluoroelastomers and fluorosolicone rubbers, polyesters, and ptfe, etc.). The leaflets can also be provided with a drug or bioagent coating to improve performance, prevent thrombus formation and promote endotheliolization. The leaflet(s) on the mitral device can also be treated or be provided with a surface layer/coating to prevent calcification. The cover on the valve body and the leaflet supporting structure can also be a combined layer from fabric and tissue, if desired. For example, the upper portion of the cover can be made from fabric, while the lower portion can be made from tissue, or vice versa. The atrial portion of the device and the body of the leaflet supporting structure can be either fully or partially covered by fabric or tissue to provide improved sealing effect and healing effect. The anchoring feature(s) built on the device can be fully or partially covered by fabric or tissue to promote tissue growth, to prevent Perivalunaer leakage (PVL), and to reduce the potential damage to the surrounding internal heart structure.

The leaflet(s) can be integrated into the leaflet supporting structure by mechanical interweaving, suture sewing, and chemical, physical, or adhesive bonding methods. The leaflet(s) can also be formed from the elements of the supporting structure. For example, the leaflet supporting structure and leaflet(s) can be directly molded and formed together from polymer or metal material. The leaflet(s) can also be formed by vapor deposition, sputtering, reflow, dipping, casting, extrusion processes or other mechanisms for attaching two or more materials together.

The tissue leaflet(s) can also be coated with drug(s) or other bioagents to prevent the formation of clots in the heart. Anti-calcification materials can also be coated or provided on the surface to prevent calcification.

FIGS. 1-5 illustrate a first embodiment of a mitral valve device 20 according to the present invention. The device 20 has an atrial flange 22, an annulus support 24, a neck section 26 that connects the atrial flange 22 to the annulus support 24, and a valve body 28 that functions as a leaflet supporting structure. Each of these components is defined by struts that define cells that in turn make up a cellular matrix.

The atrial flange 22, the annulus support 24 and the valve body 28 can be made from either a Nitinol superelastic material or stainless steel, Co—Cr based alloy, Titanium and its alloys, and other balloon expandable biocompatible materials, Other polymer biocompatible materials can also be used to fabricate these components of the device 20. In use, the device 20 can be folded or compacted into a delivery system and delivered to the location of the mitral valve through transcatheter delivery (e.g., transfemoral or transapical). Once at the location of the mitral valve, the device 20 can be released from the delivery system and positioned at the mitral valve annulus area. The atrial flange 22 can be placed at or on the native annulus of the mitral valve, with a portion of the atrial flange 22 extending inside the left atrium. See FIG. 5B. The atrial flange 22 can have a surface area that is equal or larger than the mitral annulus area. In use, the atrial flange 22 can be covered by biocompatible polymer fabric, tissue or other biocompatible materials to provide a sealing effect around the device 20 and to promote tissue growth and speed up the healing effect.

The annulus support 24 functions as an anchoring feature, and can interact with the annulus, native leaflet(s), and other internal heart structures, or subvalvular structures, to provide the desired anchoring effect. See FIG. 5B. In addition to the anchoring effect provided by the annulus support 24, the "clipping effect" created by the atrial flange 22 and the annulus support 24 can also help the device 20 to self-align and to resist potential migration during cardiac cycle. During the release of the device 20 from the delivery system, the components of the device 20 will be released out of the delivery system in sequence. For example, during transapical delivery, the atrial flange 22 will be deployed from the delivery system first, then the annulus support 24. In contrast, during transfemoral (trans-septal) delivery, the annulus support 24 will be deployed first, then the atrial flange 22. The procedures can be performed under the guidance from x-ray and/or TEE, ICE, etc.

Figure 4:
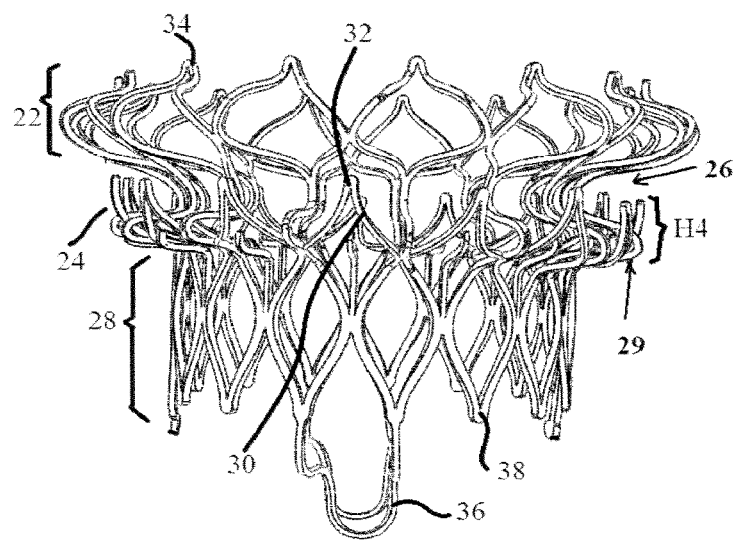
FIG. 4 is a side view of the device of FIG. 1.

FIGS. 4 and 5A illustrate the typical dimensional or geometry range for each component of the device 20. The atrial flange 22 can either have a circular profile or a profile different from a full circle. Where the atrial flange 22 has a circular profile, the diameter of the atrial portion can be in the range from 20 mm to 70 mm. If the atrial flange 22 has a profile which is different from full circle, the long axis can be in the range from 20-70 mm, and the shorter axis can be in the range from 15-65 mm. In addition, the height H1 of the atrial flange 22 can range from 0.5 mm to 20 mm. At the upper atrial end of the atrial flange 22, each cell that defines the atrial flange 22 has peaks and valleys, with a rounded non-traumatic tip 34 at each peak thereof. The angle $\ominus 1$ of the atrial flange 22 in relation to the axis of the valve body 28 can be in the range from 0 to 150 degrees. The atrial flange 22 can be either fully or partially covered by fabric or tissue material, or a combination of tissue and fabric materials. The atrial flange 22 can have barbs or spikes at the side that faces the floor of the atrium to help engage the atrial tissue and/or the annulus. The valve body 28 can have a height H3 in the range from 2 mm to 30 mm. The end of the valve body 28 that is closer to the atrium side can be higher and extrude above the atrial flange 22 to reduce the length of the valve body 28 inside the ventricle. The cross-sectional profile of the valve body 28 can either be a full circular shape or a profile that is different from a circular shape. Where the valve body 28 has a full circular profile, its diameter can be in the range from 15 mm to 50 mm. Where the valve body 28 has a profile which is different from a circular shape, the long axis can be in the range from 15 mm to 50 mm, and the shorter axis can be in the range from 10-45 mm. The valve body 28 can also have a variable profile along its height. For example, the portion of the valve body 28 near the atrial flange 22 can have an oval-shaped profile or some other profile which is different from a full circle, while the portion of the valve body 28 further away from the atrial flange 22 can have a full circular profile. The tissue leaflet(s) can be integrated into the valve body 28 either fully in the circular portion or encompass both circular and non-circular portions. The valve body 28 can be either fully or partially covered by fabric or tissue material, or a combination of tissue and fabric materials. For example, the upper portion of the valve body 28 can be covered by fabric, and the lower portion of the valve body 28 can be covered by tissue, or vice versa. In use, the fabric material and tissue can either be sewn/connected together first, or sewn/connected individually onto the valve body 28. The valve body 28 can be covered either along one surface (i.e., internal or external surface), or along both surfaces (i.e., internal and external surface). At the bottom end of the valve body 28, each cell that defines the valve body 28 has peaks and valleys, with a rounded non-traumatic tip 38 at the bottom thereof.

An optional smaller diameter neck 26 provides a transition from the atrial flange 22 to the annulus support 24. When the device 20 is in the deployed configuration, the neck 26 extends radially inwardly from the atrial flange 22 to form a U-shaped neck 26. The cross-sectional profile of the neck 26 can either be a full circular shape or a profile that is different from a circular shape. Where the neck 26 has a full circular profile, its diameter can be in the range from 15 mm to 50 mm. so Where the neck 26 has a profile which is different from a circular shape, the long axis can be in the range from 15 mm to 50 mm, and the shorter axis can be in the range from 10 mm to 45 mm.

The neck 26 then transitions radially outwardly to the annulus support 24, which comprises a ring of U-shaped sections 29 that alternate with a ring of spaced-apart inverted V-shaped tabs 30. The neck 26 actually transitions radially outwardly to the ring of U-shaped sections 29, which extend radially outwardly before extending radially inwardly to transition to the valve body 28. The tabs 30 extend radially outwardly from the valve body 28 and have a generally perpendicular upward bend to define a ring that encircles the neck 26. The number of tabs 30 ranges from 1 to 20. The cross-sectional profile of the ring of tabs 30 can either be a full circular shape or a profile that is different from a circular shape. Where the ring of tabs 30 has a full circular profile, its diameter can be in the range from 15 mm to 70 mm. Where the ring of tabs 30 has a profile which is different from a circular shape, the long axis can be in the range from 15 mm to 70 mm, and the shorter axis can be in the range from 10 mm to 65 mm. The connection point of the inverted V-shape for the tabs 30 is an enlarged point 32 whose function is to contact or press against the annulus or the native leaflet(s) of the mitral valve region of the heart to secure the device 20 at the annulus area, and therefore function as anchoring features. Each tab 30 has a height H4 that ranges from 0.5 mm to 10 mm. The tabs 30 can be either fully or partially covered by tissue or fabrics. For example, the enlarged point 32 can be uncovered by fabric/tissue, while the remainder of the annulus support 24 can be covered. Use of fabric can promote tissue in-growth and provide better securement of the device 20 at the annulus in addition to providing additional sealing effect to prevent Perivalvular leakage (PVL).

Thus, the ring of U-shaped sections 29 has a diameter that is greater than the diameter of the valve body 28 and the neck 26, but less than the diameter of the atrial flange 22. Similarly, the ring of tabs 30 has a diameter that is greater than the diameter of the valve body 28 and the neck 26, but less than the diameter of the atrial flange 22. The tabs 30 and U-shaped sections 29 can be arranged to alternate each other in the same general ring, and can have diameters that are about the same as each other.

Two U-shaped tails 36 can extend from the valve body 28 at the end of the valve body 28. Even though two tails 36 are shown, it is possible to provide the device 20 with only one tail 36, or three or more tails 36. As best shown in FIG. 5A, each tail 36 can be formed by extending from two lower tips 38 of the valve body 28 to join a U-shaped bottom, and is used to allow a suture or other string to be tied thereto so that the suture or string can be used to adjust the position of the device 20 during deployment thereof. The tails 36 can also be connected with some features in the delivery system to help with (1) valve loading (i.e., loading the valve into the delivery system sheath): and (2) valve positioning at the annulus region of the heart. With regards to valve positioning, the tails 36 help to adjust the position and/or the angle of the device 20 before the final release of the device 20 from the delivery system during deployment. Another advantage to having the tail(s) 36 is that before the device 20 is completely deployed and released from the delivery system, the device 20 would normally already start to function (partially or fully), so this gives the physician more time to adjust the position and suspend the device 20 before it is finally disconnected from the delivery system. The length of each tail 36 can range from 5 mm to 25 mm. The tail can be shape-set and bent into a shape, so that the tail(s) 36 can be extended away from the circular profile defined by the valve body 28 if desired. For example, the tail 36 can suspend from the distal end of the valve body 28, and bend inwardly toward the lumen of the valve body 28.

Figure 7A:
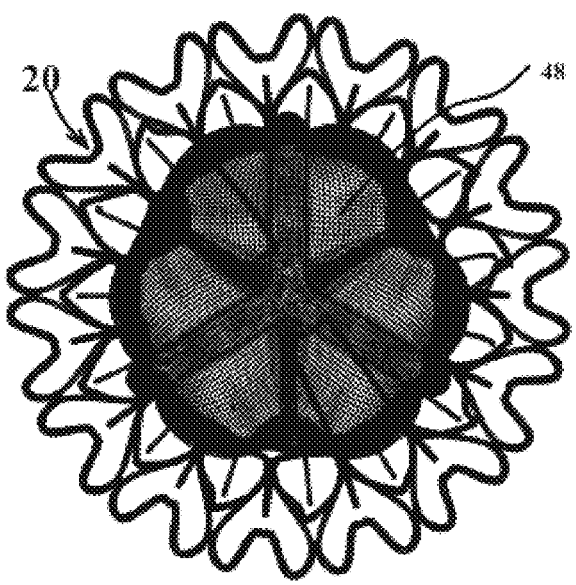
FIG. 7A is top view of an assembled mitral valve replacement device that includes the leaflets incorporated with the device of FIG. 1, with the leaflets in the opened position.
Figure 7B:
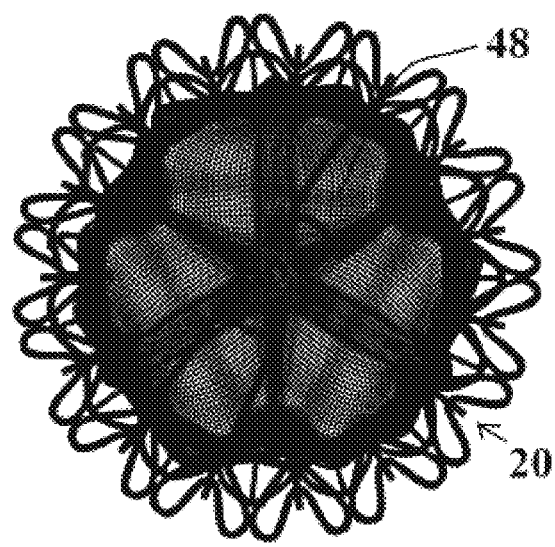
FIG. 7B is a bottom view of the assembled mitral valve replacement device of FIG. 7A with the leaflets in the opened position.

Referring to FIG. 5B, when the device 20 is deployed in use at the location of a native mitral valve location, the tabs 30 are deployed and "seat" at/on the annulus, with a portion of the atrial flange 22 extending inside the left atrium. This interaction of the atrial flange 22 (from above) and the tabs 30 (from below) provide a "clipping effect" that is effective in securing the device 20 at the desired location. When the device 20 is deployed, the U-shaped sections 29 can positioned at a location just below the annulus, to provide an additional sealing effect. The struts/cell space in the atrium can be fully, or partially, or not covered, by fabric and/or tissue. By providing the atrial flange 22 in a partially or non-covered arrangement inside the atrium, the interference to the forward blood flow can be minimized. The tissue leaflet(s) 48 of the device 20 is/are integrated into the valve body 28 to replace the function of the native mitral leaflets. As shown in FIG. 7A and 7B, the native leaflets are positioned adjacent to, and at the outside surface of, the valve body 28.

Figure 6A:
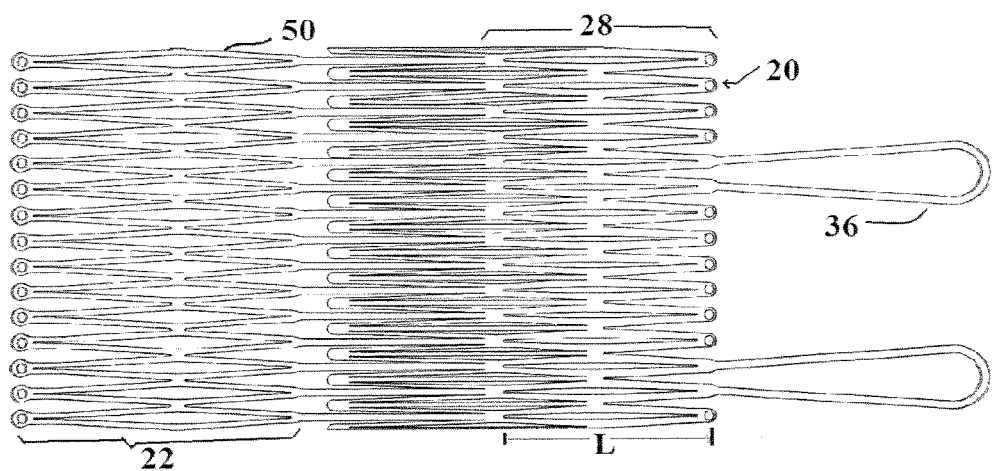
FIG. 6A illustrates the two-dimensional flat configuration of the device of FIG. 1 after it has been laser cut from metal or polymer tubing.
Figure 6B:
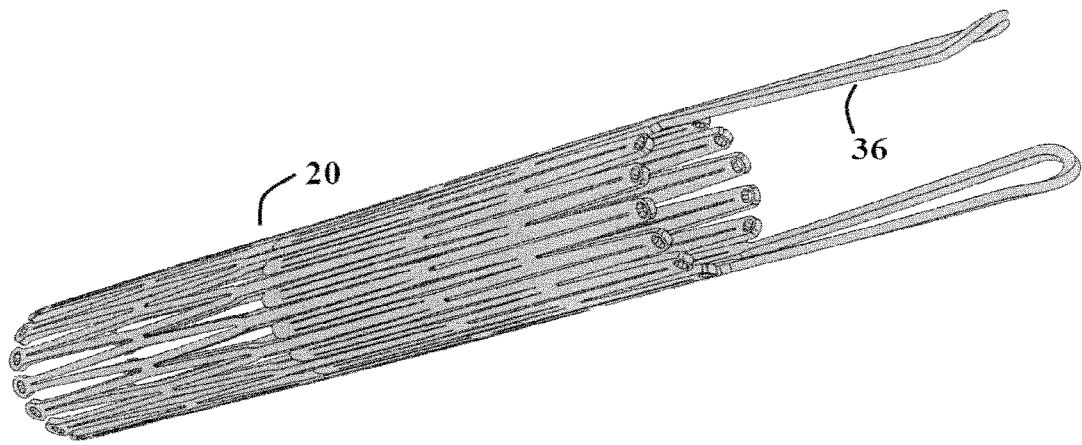
FIG. 6B is a perspective three-dimensional view of the device laser-cut pattern shown in FIG. 6A, prior to forming the final shape as shown in FIG. 1. The device in its final shape can be integrated with the tissue leaflet(s) and skirt(s), can be compacted into a smaller profile, and loaded into a delivery system.

FIGS. 6A-6B show the exemplary laser cut configuration of the device 20. The device 20 can be laser cut from metal or polymer tubing to reach the configuration shown in FIG. 6A. The cut structure would then go through shape setting, micro-blasting, and electro-polishing processes to achieve the desired profile/shape, as shown in FIGS. 1-5B. The width of each strut 50 can range from 0.2 mm to 1.5 mm, and the thickness of each strut 50 can range from 0.2 mm to 0.75 mm. The length of each cell can be in the range from 2 mm to 20 mm. The number of rings along the length of the device 20 can range from 2 to 20. The number of cells along the circumference of the device 20 can range from 2 to 20. As an alternative, the device 20 can also be fabricated from flat sheet, and then rolled to the desired shape. The device 20 can be delivered according to more than one delivery method. For example, a transapical delivery can be used where the atrial flange 22 can be deployed first, and provide tactile feedback during the delivery procedure. The annulus support 24 (i.e., tabs 30) will be released and deployed last to complete the implantation of the device 20. During a transfemoral/transseptal delivery, the tabs 30 can be deployed first, and provide tactile feedback during the delivery procedure. The atrial flange 22 will be released and deployed last to complete the implantation of the device 20. During the delivery, the tabs 30 can be bent inward (either up and inward, or down and inward) towards the valve body 28. When the tabs 30 are released/deployed, they can expand and press against the valve annulus or native leaflet(s).

Figure 8A:
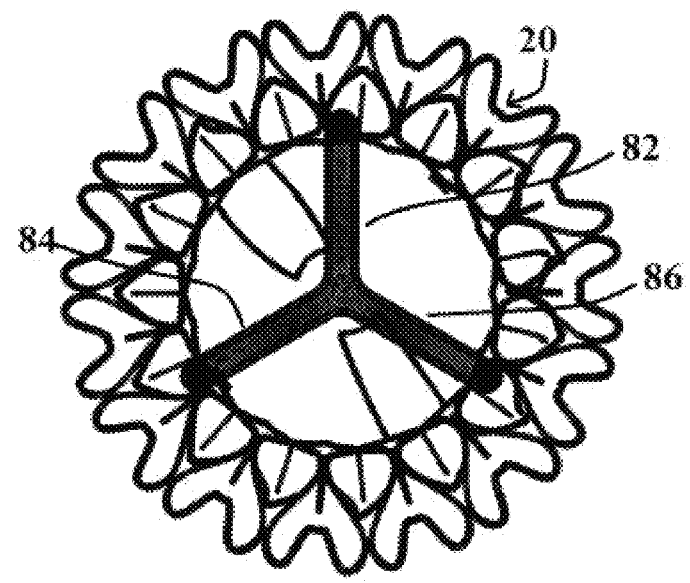
FIG. 8A is top view of an assembled mitral valve replacement device that includes the leaflets incorporated with the device of FIG. 1, with the leaflets in the closed position.
Figure 8B:
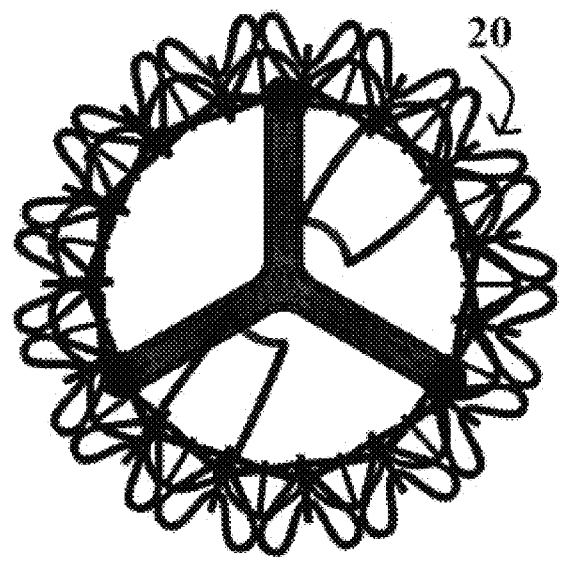
FIG. 8B is a bottom view of the assembled mitral valve replacement device of FIG. 8A with the leaflets in the closed position.
Figure 9A:
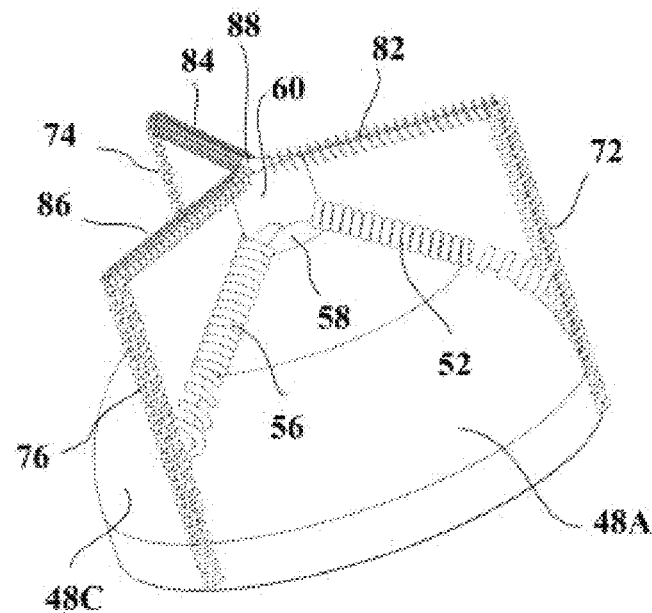
FIG. 9A is a perspective view of the leaflet assembly of FIG. 7A when the leaflets are opened, with the mitral valve closed.
Figure 9B:
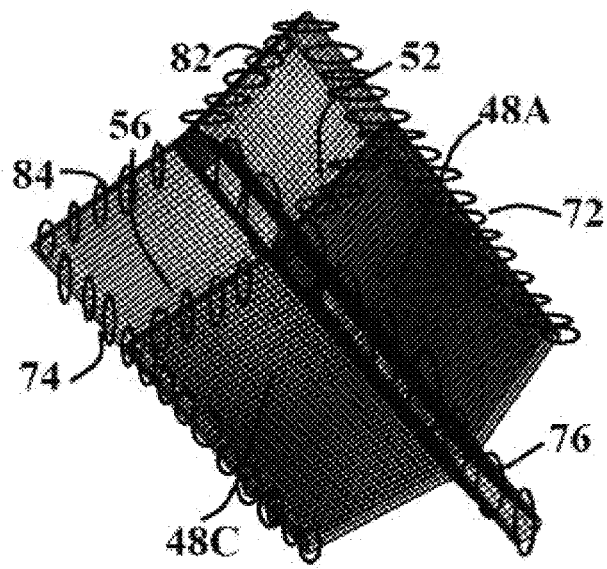
FIG. 9B is a perspective view of the leaflet assembly of FIG. 7A when the leaflets are closed, with the mitral valve opened.
Figure 10A:
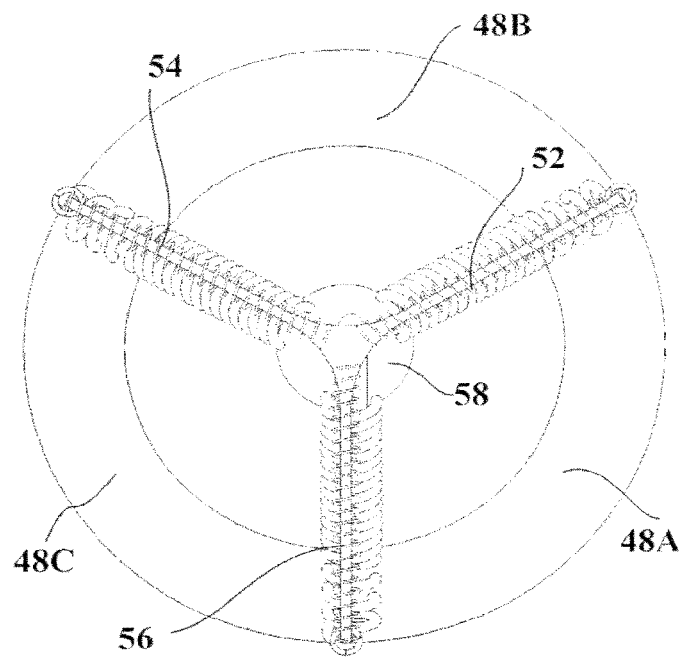
FIG. 10A is a top view of the leaflet assembly of FIG. 7A when the leaflets are opened, with the mitral valve closed.
Figure 10B:
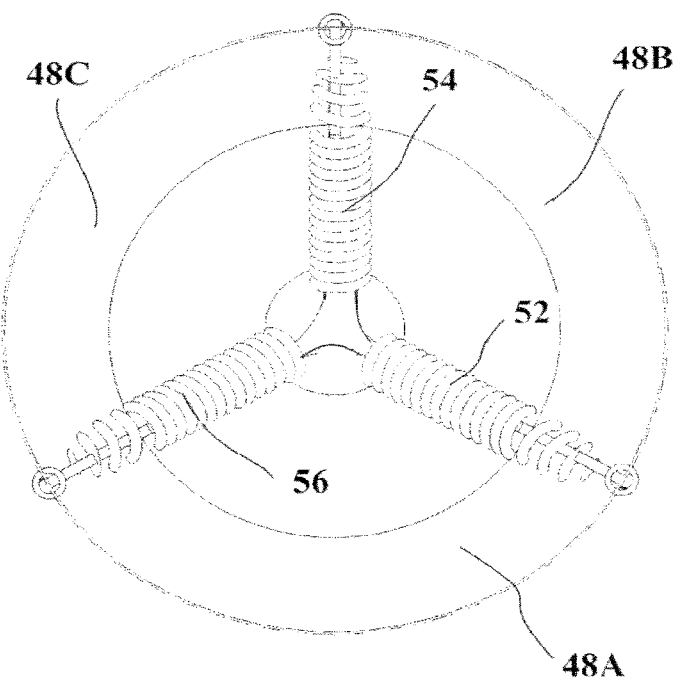
FIG. 10B is a bottom view of the leaflet assembly of FIG. 7A when the leaflets are opened, with the mitral valve closed.
Figure 11:
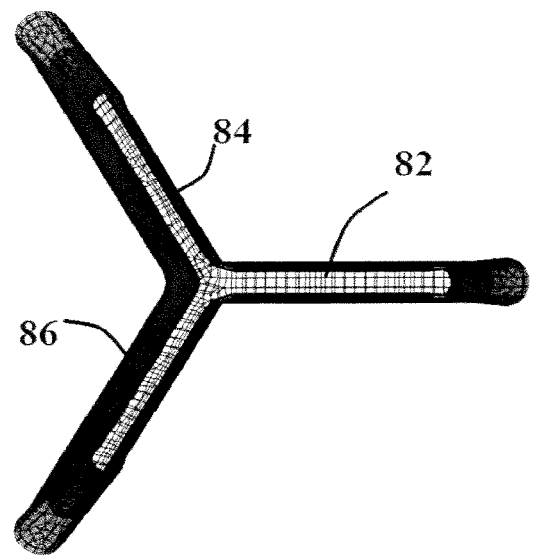
FIG. 11 is a top view of the leaflet assembly of FIG. 7A when the leaflets are closed, with the mitral valve opened.

In use, the device 20 can be compacted into a smaller profile for easy delivery and can be delivered and deployed once it reaches the target implant site. The compacted device profile can be less than 48 Fr, with 15 Fr to 40 Fr being the typical range for such applications FIG. 7A shows a top view of an assembled mitral valve replacement device that includes the leaflets 48 incorporated with the mitral device 20 described above. FIG. 7B shows a bottom view of the assembly of FIG. 7A. FIGS. 7A and 7B show the leaflets 48 in an opened position, so that blood flow from the left ventricle to the left atrium is prevented. The coaption area is between the leaflets 48 and the skirt defined by the device 20 along the internal lumen of the device 20 in the valve body 28. Similarly, FIGS. 8A and 8B are top and bottom views, respectively, of the assembled mitral valve device of FIGS. 7A and 7B, showing the leaflets 48 in a closed position, so that blood can flow from the left atrium to the left ventricle. As best shown in FIGS. 7A-8B, and also in FIGS. 9A-11, the present invention also provides a novel leaflet configuration. The leaflets 48 have a configuration that is essentially the opposite of the natural leaflet configuration, such that the valve leaflets 48 open inwardly and close by expanding outwardly to contact the inner surface of the valve body 28. The leaflets 48 are attached to the device 20 in a manner which allows the leaflets to freely close inward to allow forward blood flow through the valve device. The height (depth) of the tissue leaflet(s) can vary from 2-30 mm, depending on the anatomy of the heart.

The leaflet structure is best shown in FIGS. 7A-11, and this embodiment shows the use of the three leaflets 48A, 48B and 48C that have been sewn together along three longitudinal stitch or suture lines 72, 74 and 76. The stitch lines 72, 74, 76 extend along outer edges of the leaflets 48A, 48B and 48C, and also form junction lines where the leaflet structure is connected to the valve body 28. The leaflets 48A, 48B and 48C are sewn along their edges to the struts 50 that make up the valve body 28. At the top (atrial) edge of the leaflets 48A, 48B and 48C, radial stitch or suture lines 82, 84 and 86 extend from the longitudinal stitch lines 72, 74 and 76, respectively, towards a central point 88 where a flat tip 60 is located. Three inner stitch or suture lines 52, 54 and 56 originate from an apex 58 where the atrial edge of the leaflets 48A, 48B, 48C are crimped together to form the central flat tip 60, so that the starting point of the stitch lines 52, 54, 56 are offset from the stitch lines 82, 84, 86. Each stitch line 52, 54, 56 extends for a short distance towards the respective stitch lines 72, 74 and 76, and merge with the stitch lines 72, 74 and 76, respectively. This arrangement of stitch or suture lines allows the three leaflets 48A, 48B and 48C to form an umbrella-shaped configuration for its valvular structure where the leaflets 48A, 48B, 48C will not open all the way to the top (atrial) stitch lines 82, 84, 86 under ventricular pressure to prevent the leaflet(s) from flipping over, and to minimize leakages. The distance between the domed ceiling defined by the leaflets 48A, 48B, 48C and the top (atrial) stitch lines 82, 84, 86 is between 0.25 mm and 10 mm. The leaflet structure inside the device 20 can be made using multiple leaflets 48 (as shown and described above) or a single leaflet 48. In the case of a single leaflet, the single piece of leaflet 48 can be folded and sewn to the shapes shown in FIGS. 7A-11 above.

Thus, the novel leaflet design of the present invention uses the reverse leaflet action to regulate the blood flow between the left atrium and left ventricle. This reverse or "umbrella-" or "balloon-like" leaflet(s) design provides better sealing/coaptation, and also improves fatigue performance of the valve body 28 by eliminating the contraction/squeezing force/deformation that typically acts on the valve body 28 using a conventional leaflet design.

Figure 12:
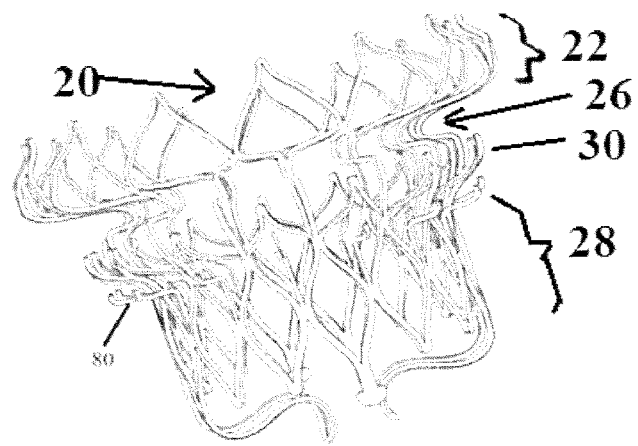
FIG. 12 is a perspective view of a mitral valve device according to a second embodiment of the present invention.
Figure 13:
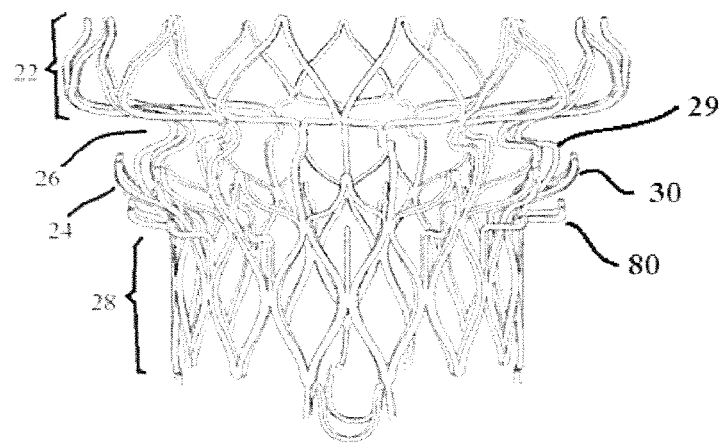
FIG. 13 is a side view of the device of FIG. 12.
Figure 14:
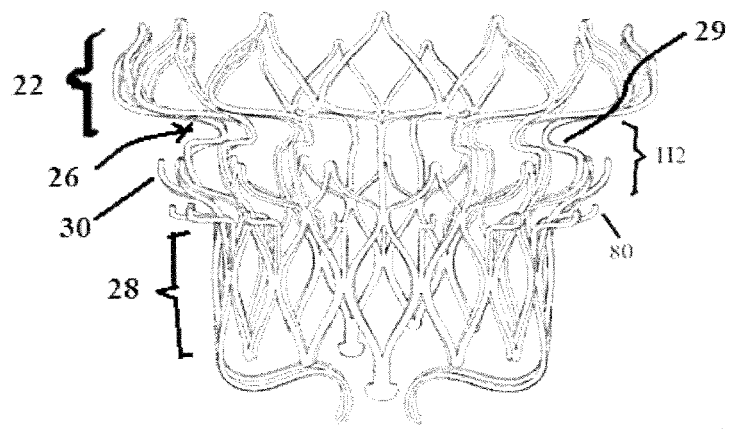
FIG. 14 is another side view of the device of FIG. 12 which is rotated by 90 degrees from the view of FIG. 13.

FIGS. 12-14 illustrate a second embodiment of a mitral valve device 20 according to the present invention, which includes the addition of clips 80. The device 20 in FIGS. 12-14 also have an atrial flange 22, an annulus support 24, a neck section 26 that connects the atrial flange 22 to the annulus support 24, and a valve body 28 that functions as a leaflet supporting structure, all of which can be the same as the corresponding elements in FIGS. 1-5. Each of these components is also defined by struts that define cells that in turn make up a cellular matrix.

Figure 15:
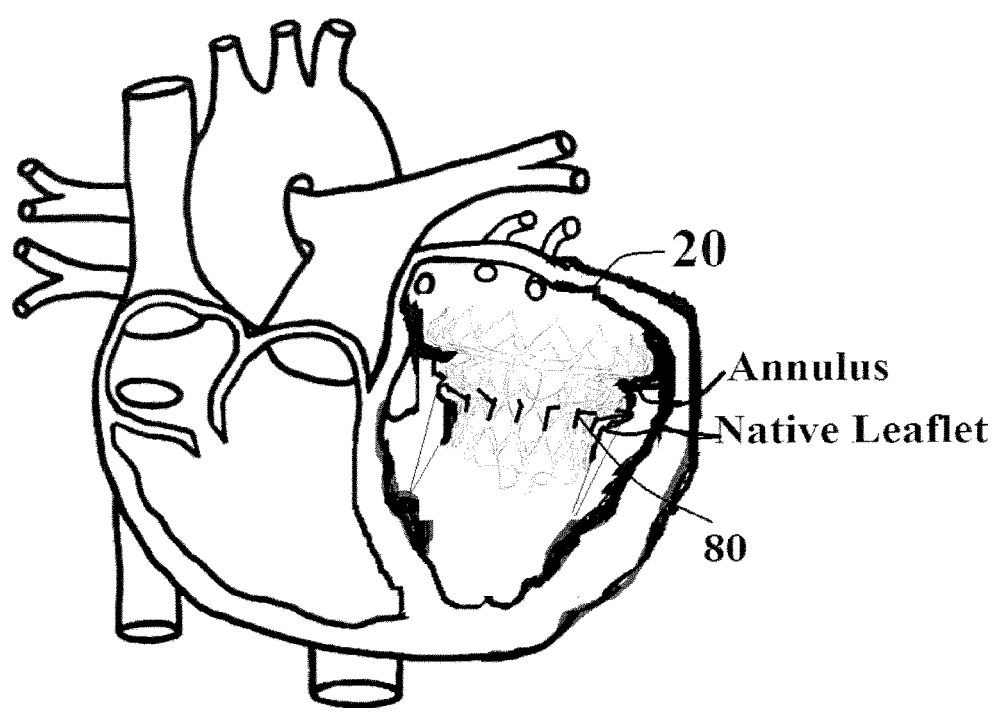
FIG. 15 illustrates the device of FIG. 12 positioned at the mitral valve annulus of a human heart.

The difference between the two embodiments is the addition of a ring of clips 80 that are provided in spaced-apart manner around the valve body 28 at a location spaced vertically below the annulus support 24. These clips 80 are somewhat L-shaped in that each clip 80 can extend vertically from any of the struts in the valve body 28, then horizontally in a radial direction before terminating in a short bend at its tip. The clips 80 function to clip or hold a portion of the native leaflet after the device 20 has been deployed, as best shown in FIG. 15. This clipping function improves the securement of the device 20 the annulus region of the mitral valve area. The clipping effect provided by the atrial flange 22 and the tabs 30 is also in play here, but the clips 80 provide improved securement. The height H2 defines the combined height of the neck 26 and the annulus support 24, and can also be varied to accommodate for the clips 80, and can range from 0 mm to 10 mm.

Once the device 20 is implanted, the atrial flange 22, the valve body 28 and the anchoring mechanisms (e.g., the clipping effect of the atrial flange and the tabs 30; the addition of the clips 80) built into it or created by the interaction of the device 20 with native leaflet(s) and other internal heart structure (or other subvalvular structures) will maintain the device 20 in the desired position. During ventricular systole, when the valve created by the leaflet(s) 48 and the valve body 28 is closed, the pressure from the left ventricle will generate an uplifting force and trying to push the device 20 up toward the atrium. That is one of the reasons why a reliable and adequate anchoring mechanism is needed to maintain the device 20 in position after the device 20 is implanted. For example, during heart contraction, the tissue leaflet(s) 48 will close the valve lumen, so that the blood will be pumped toward the aortic valve to the aorta. In the mean time, the native leaflet(s) move up (inward) toward the outside surface of the valve body 28 (wrap around), and try to seal/close the mitral valve to prevent PVL. The anchoring feature(s) built in the device 20 can engage the native leaflet(s) and other internal heart structure to prevent the device 20 from being pushed upward. During heart relaxation, the tissue leaflet(s) 48 on the device 20 will turn to a smaller profile to allow the blood to flow through and fill the left ventricle. The tissue leaflet(s) 48 can be operated (opened or closed) by the combined effect of blood flow, cardiac pressure, and cyclic-pulsatile movement of the supporting structure during the cardiac cycle.

In addition to the anchoring effect of the anchoring mechanisms (annulus support 24 and tabs 30), the pressure applied on to the valve body 28 by the native leaflet(s) during ventricular systole can also help to keep the device 20 from moving upward to the atrium by applying a clamping force onto the device 20. This is a dynamic anchoring mechanism and it takes effect only during the ventricular systole, at which stage, the device 20 under the highest uplifting force trying to push the device 20 up toward the atrium direction. This additional dynamic anchoring effect helps to maintain the proper position of the device 20 and reduces the anchoring force and its duration acting onto the native heart anatomy. Over time, tissue growth/healing would connect/fuse the native leaflet(s) onto the valve body 28.

FIGS. 16-22 illustrate a third embodiment of a mitral valve device 20a according to the present invention. The device 20a in FIGS. 16-22 also has an atrial flange 22a, an annulus support 24a, and a neck section 26a that connects the atrial flange 22a to the annulus support 24a. The valve body VB is now defined by the atrial flange 22a, the annulus support 24a, and a ventricular portion that is defined by V-shaped tabs 28a.

The atrial flange 22a is similar to the atrial flange 22, except that the atrial flange 22a may have a lower profile. A ring of spaced-apart inverted V-shaped tabs 34a defines peaks and valleys for the atrial flange 22a, with a rounded non-traumatic tip 35a at each peak thereof. A plurality of leaflet holders or posts 37a extends from selected tips 35a, and each functions to support and hold portions of the leaflet. Each post 37a can be straight or curved.

The atrial flange 22a can be placed at or on the native annulus of the mitral valve, with a portion of the atrial flange 22a extending inside the left atrium. See FIG. 20. The atrial flange 22a can have a surface area that is equal or larger than the mitral annulus area. In use, the atrial flange 22a can be covered by biocompatible polymer fabric, tissue or other biocompatible materials to provide a sealing effect around the device 20a and to promote tissue growth and speed up the healing effect.

The atrial flange 22a can either have a circular profile or a profile different from a full circle (e.g., D-shaped or oval). Where the atrial flange 22a has a circular profile, the diameter of the atrial portion can be in the range from 12 mm to 75 mm. If the atrial flange 22a has a profile which is different from full circle, the long axis can be in the range from 12 mm to 75 mm, and the shorter axis can be in the range from 6 mm to 70 mm. In addition, the height H11 of the atrial flange 22a can range from 0.5 mm to 30 mm. The atrial flange 22a can be either fully or partially covered by fabric or tissue material, or a combination of tissue and fabric materials.

The annulus support 24a functions as an anchoring feature, and can interact with the annulus, native leaflet(s), and other internal heart structures, or subvalvular structures, to provide the desired anchoring effect. In addition to the anchoring effect provided by the annulus support 24a, the "clipping effect" created by the atrial flange 22a and the anchors 29a (explained below) can also help the device 20a to self-align and to resist potential migration during cardiac cycle. During the release of the device 20a from the delivery system, the components of the device 20a will be released out of the delivery system in sequence. For example, during transapical delivery, the atrial flange 22a will be deployed from the delivery system first, then the annulus support 24a, or vice versa. In contrast, during transfemoral (trans-septal) delivery, the annulus support 24a will be deployed first, then the atrial flange 22a. The procedures can be performed under the guidance from x-ray and/or TEE, ICE, etc.

The neck 26a transitions from the flange 22a radially outwardly to the annulus support 24a, which comprises a ring of anchors 29a. The neck 26a actually transitions radially outwardly to the ring of anchors 29a, which extend radially outwardly before extending radially inwardly to transition to the V-shaped tabs 28a that extend into the ventricular portion. The number of anchors 29a ranges from 1 to 20. The cross-sectional profile of the ring of anchors 29a can either be a full circular shape or a profile (e.g., oval or D-shaped) that is different from a circular shape. Where the ring of anchors 29a has a full circular profile, its diameter can be in the range from 10 mm to 75 mm. Where the ring of anchors 29a has a profile which is different from a circular shape, the long axis can be in the range from 10 mm to 75 mm, and the shorter axis can be in the range from 5 mm to 70 mm. An annular clipping space is defined between the ring of anchors 29a and the atrial flange 22a, and this clipping space has a height H14 (see FIG. 19) that can be in the range from 0.5 mm to 30 mm. Each anchor 29a ends in a rounded tip 32a whose function is to contact or press against the annulus or the native leaflet(s) of the mitral valve region of the heart to secure the device 20a at the annulus area, and therefore function as anchoring features. Each anchor 29a can be either fully or partially covered by tissue or fabrics. Thus, the ring of anchors 29a has a diameter that is greater than the diameter of the valve body VB and the neck 26a, but can be less than, equal to, or even greater than the diameter of the atrial flange 22a.

Figure 19:
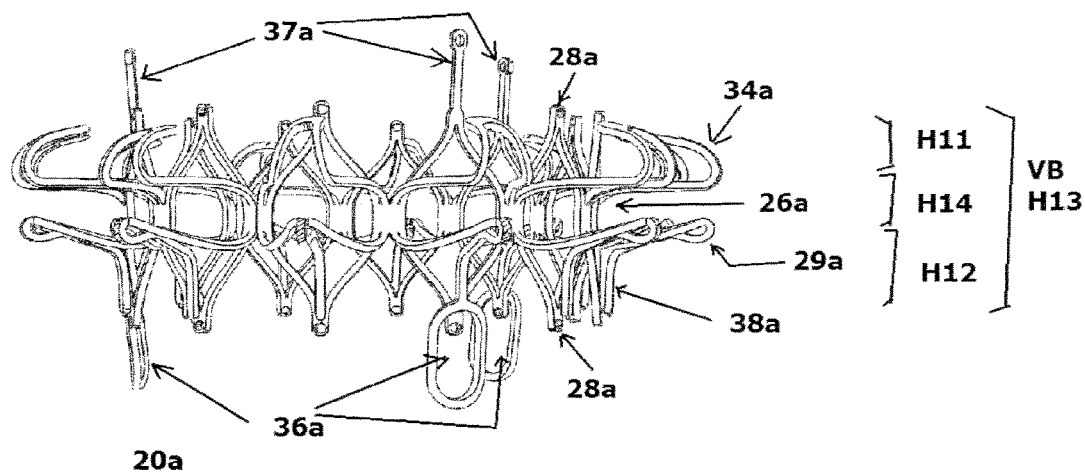
FIG. 19 is a side view of the device of FIG. 16.
Figure 20:
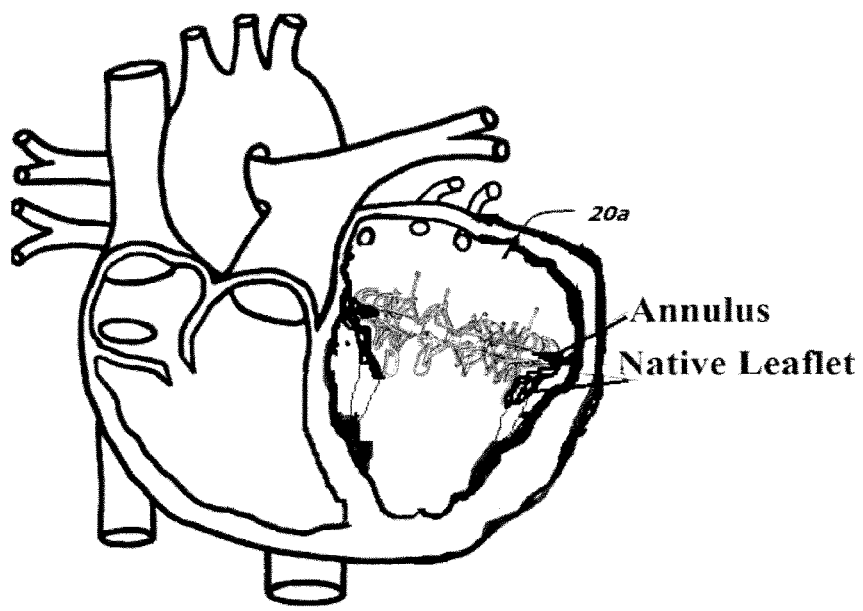
FIG. 20 illustrates the device of FIG. 16 positioned at the mitral valve annulus of a human heart.
Figure 21:
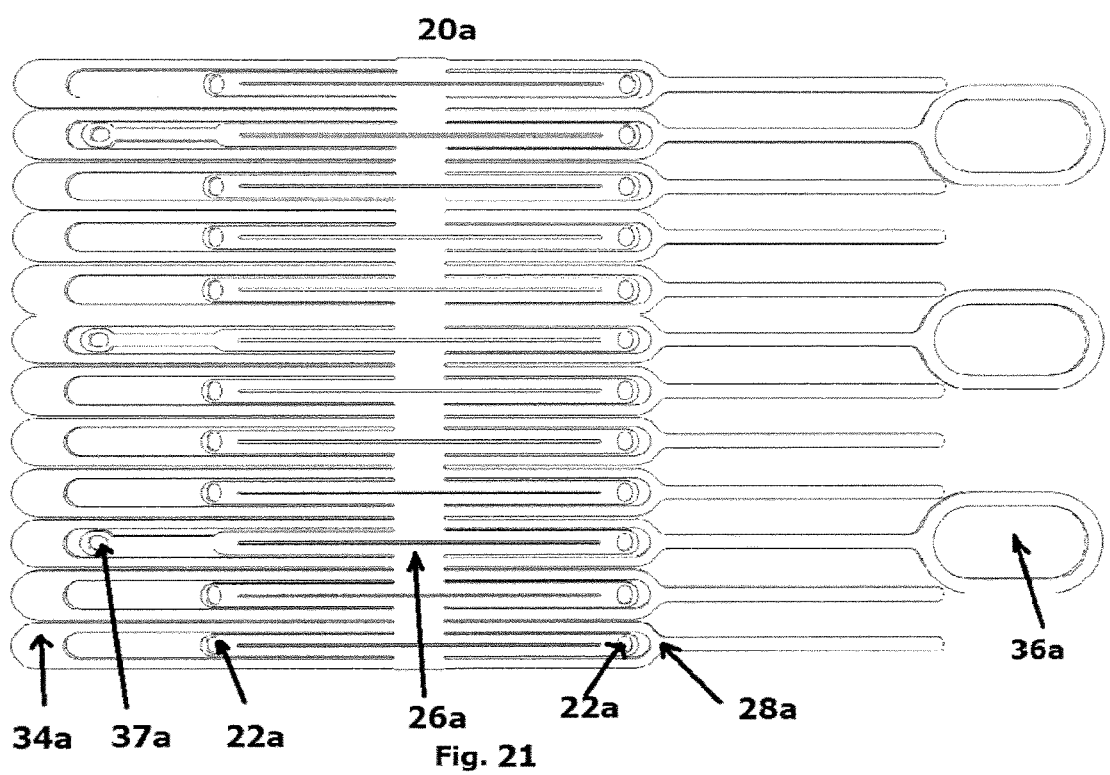
FIG. 21 illustrates the two-dimensional flat configuration of the device of FIG. 16 after it has been laser cut from metal or polymer tubing.
Figure 22:
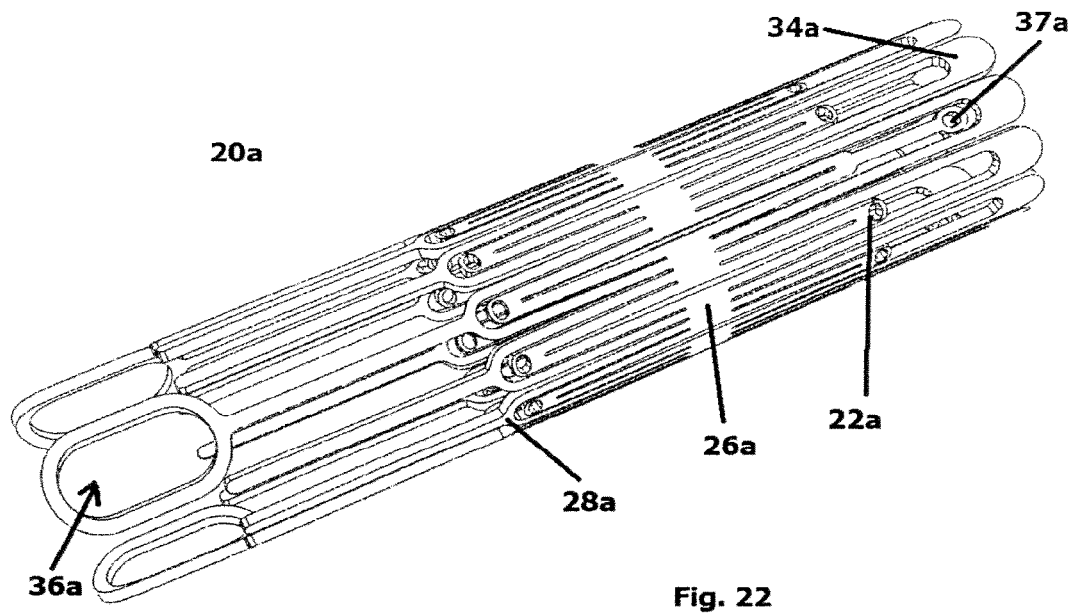
FIG. 22 is a perspective three-dimensional view of the device laser-cut pattern shown in FIG. 21, prior to forming the final shape as shown in FIG. 16. The device in its final shape can be integrated with the tissue leaflet(s) and skirt(s), can be compacted into a smaller profile, and loaded into a delivery system.

A plurality of enclosed valve holders 36a can extend from the V-shaped tabs 28a at the end of the ventricular portion. Even though a specific number of holders 36a are shown, it is possible to provide the device 20a with any number, ranging from one or more holders 36a. As best shown in FIGS. 16, 19 and 21, each holder 36a is connected to the tip 38a of a corresponding V-shaped tab 28a. The holders 36a are provided for performing the same functions as the tails 36. The length of each holder 36a can range from 5 mm to 25 mm.

The ventricular portion can have a height H12 in the range from 2 mm to 15 mm. Thus, the combined valve body VB can have a height H13 in the range from 4 mm to 30 mm, and preferably between 8 mm to 20 mm. The cross-sectional profile of the ventricular portion can either be a full circular shape or a profile (e.g., oval or D-shaped) that is different from a circular shape. Where the ventricular portion has a full circular profile, its diameter can be in the range from 10 mm to 75 mm. Where the ventricular portion has a profile which is different from a circular shape, the long axis can be in the range from 10 mm to 75 mm, and the shorter axis can be in the range from 5 mm to 70 mm. The ventricular portion can also have a variable profile along its height. For example, the portion of the ventricular portion near the annulus support 24a can have an oval-shaped profile or some other profile which is different from a full circle, while the portion of the ventricular portion further away from the annulus support 24a can have a full circular profile. Also, once implanted, the ventricular portion can be positioned in the left ventricle only, in the left atrium only, or in both the left atrium and the left ventricle.

An important aspect of this embodiment is the shortened length (i.e., height H12) of the ventricular portion, resulting in a device 20a that has a shorter profile than conventional valve replacement devices. The shorter profile is beneficial in that it minimizes the potential LVOT obstruction to facilitate better cardiac output. In addition, the shorter profile minimizes the interference with the cardiac structures in the left ventricle, such as the chordaes, and the papalary muscles, among others.

Figure 23:
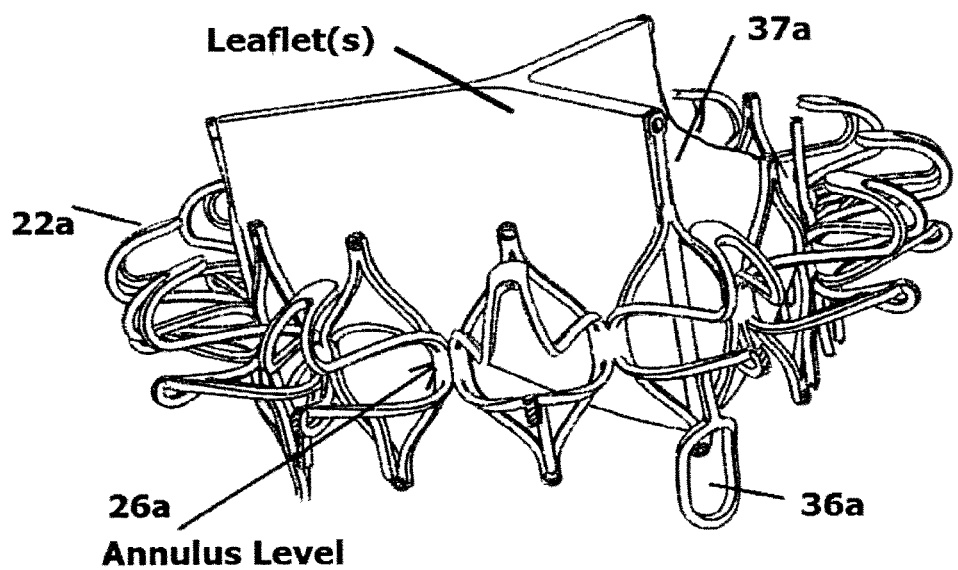
FIG. 23 illustrates the location of the leaflets of the device of FIG. 16 within the left atrium of the patient.

As a result of the shortened profile, the tissue leaflet(s) are positioned primarily within the atrial flange 22 and above the atrial flange 22 (see FIG. 23), so that the posts 37a can be used to hold or connect the upper portions of the leaflet(s). The leaflet(s) can also be integrated into the valve body VB either fully in the circular portion, or encompassing both circular and non-circular portions. The valve body VB can be either fully or partially covered by fabric or tissue material, or a combination of tissue and fabric materials. For example, the inner surface of the valve body VB can be covered by fabric, and the outer surface can be covered by tissue, or vice versa. In use, the fabric material and tissue can either be sewn/connected together first, or sewn/connected individually onto the valve body VB. The valve body VB can be covered either along one surface (i.e., internal or external surface), or along both surfaces (i.e., internal and external surface).

During transapical delivery, the ventricular portion and the holders 36a can be pulled straight and inserted into a delivery system. When deployed, the annulus support 24a is deployed either at the level of the native annulus or a level below the native annulus, and engages the native valvular structure through the dipping effect created by clipping the native annulus and/or native leaflets between the atrial flange 22a and the anchors 29a. See FIG. 20. To deploy the device 20a, the atrial flange 22a is first deployed in the left atrium, and then the ventricular portion is deployed in the left ventricle (or vice versa) so that the device 20a and its leaflet assembly can experience partial or full leaflet function. Next, the tabs 38a without the holder 36a are released/deployed so that the annulus ring 24a can be firmly retained at the location of the native annulus. Finally, the device 20a is manipulated to adjust its position, and then the tabs 38a with the holders 36a are released/deployed. This staged deployment action provides more accurate valve positioning and improved anchoring effect.

The device 20a can be used for mitral valve replacement, or aortic valve replacement. For mitral valve replacement, the leaflet(s) can be positioned above, at or below the native annulus. For aortic valve replacement, the leaflet(s) can be positioned at or above the native annulus.

When the device 20a has been fully deployed inside the heart at the location of a mitral valve, the leaflet(s) will be positioned primarily above the location of the native annulus. See FIG. 23. The slightly high leaflet location makes it possible to reduce the length of the valve body VB length extending inside the left ventricle.

The key advantages/novelty of the device 20 of the present invention include the following:

(1) the native leaflets and other internal valvular and subvalvular structures are preserved;

(2) the device 20 treats heart regurgitation with minimum interference/obstruction with the function of native structures of the heart, such as the chordae tendineae, papillary muscles, left ventricle, LVOT, impingement on the aortic valve etc.;

(3) the design of the device 20 considers the natural geometry and anatomy of the heart valve with minimal modification to the native heart valve, the profile of the annulus, surrounding structures, and sub-valvular structures;

(4) the device 20 has a design which self-conforms to the natural contour of the heart anatomy and the sealing portion at the annulus can contract and expand like a normal natural annulus;

(5) the profile of the device 20 can be set to a shape that is other than a full circle, such as a "D"-shape, a "ɔ"-shape, or an oval shape, to correspond to the profile of nature annulus, and the portion of the device 20 that contacts near the annulus can have a "V"-shaped profile to mimic the contour of nature mitral anatomy;

(6) the anchoring features on the device 20 utilize the native leaflets and other internal valvular or subvalvular structures;

(7) the device 20 can adjust its size/profile automatically to adapt to the left ventricle size/volume change after implantation;

(8) the device 20 can have variable profiles to help create the sealing effect during ventricular systole, and also provides a clamping effect by interaction between the native leaflet(s) to help maintain device position during ventricular systole; for example, the device 20 can have a "Transition Zone" between the atrial flange 22 and value body 28. The "Transition Zone" can have a profile which is different from other portions of the device 20. One example is that the "Transition Zone" can have an oval-shaped profile instead of a full circular profile. There is a long axis and a short axis in the Transition Zone, the long axis can be arranged in a direction along "commisure-to-commisure", while the other axis is shorter than the longer axis. The oval profile in the Transition Zone can help to create an improved sealing effect at the commisure areas. The Transition Zone could also include the neck 26 to increase the "sealing" surface area. This also offers a dynamic anchoring effect to the device 20 and it takes effect during ventricular systole, at which stage the uplifting force acting on the device 20 is the highest;

(9) the device 20 has a design which uses the native leaflet(s) and chordae to provide both sealing effect and anchoring effect;

(10) the device 20 can be implanted surgically or though minimally-invasive procedures, such as transapical, transseptal, and transfemoral procedures;

(11) the tails 36 at the valve body 28 allow physicians sufficient time to adjust the valve position/angle for ideal valve performance during deployment; and

(12) the inner shaft inside the delivery system can be designed and made in a manner where it is movable during the valve deployment. For example, during delivery, once most of the device 20 is released/deployed from the delivery system, the leaflet(s) 48 on the device 20 will start to function as the heart beats. At this time, the inner shaft of the delivery system may still be inside the lumen of the device 20, and may affect the movement of one of the leaflets on the device 20. In this situation, the inner shaft in the delivery system may be loose from the proximal handle end of the delivery system, and pulled back proximally, so that the inner shaft will not be inside the lumen of the device. Therefore, all leaflet(s) 48 on the device 20 can move freely. This means that the device 20 can achieve a better valve function when the tails 36 are still connected with the delivery system. In other words, the fact that the leaflet(s) 48 on the device 20 are functioning during the deployment will give the physician more time to adjust the valve position/angle for optimal performance.

In addition to the securement mechanisms described above, adhesive bonding/interface can also be used to secure the device 20 in the native mitral position. One example is to use biocompatible glue/adhesive to connect/fix/secure the device 20 in the mitral position. In use, the biocompatible adhesive/glue can be applied on the outer surfaces of the device 20, such as along the outer surface of the valve body 28, the atrial flange 22 or any surface of the device 20 that might contact any native mitral structures, such as the annulus, the atrial surface above or on the annulus level, native leaflet(s), heart muscles, and other valvular and/or subvalvular structure(s), to maintain the position of the device 20 after implantation. Bioagents can also be added into the biocompatible adhesive/glue to promote healing and tissue growth.

The adhesive/glue can be fast reacting in nature, and form a bond with the native mitral structure instantly upon contact with the blood. It can also be actuated by heat or temperature; the heat or temperature can be generated/controlled by electrolytic heating, or FR heating, or ultrasound energy, or magnetic energy, or microwave energy, or the blood temperature itself, or chemical reaction, through the portion or entire structure of the device 20.

The adhesive/glue can be also be slow reacting in nature, and form a bond with the native mitral structure after a period of time upon contact with the blood. The time needed to form the bond can vary from 1 second to 2 hours, from 1 second to 28 hours, etc.

The adhesive/glue can also have a controlled reaction in nature, and form a bond with the native mitral structure in a controlled manner upon contact with the blood. One example of this concept is to apply a top layer (or layers) of other biocompatible materials over the adhesive/glue layer/material on the device 20. The top layer(s) of the other biocompatible material can be removed or dissolved in a controlled manner either through the use of energy, heating, chemical reaction, or mechanically, or magnetically, to ensure that the adhesive/glue underneath the top layer can effectively form the bond with the native mitral structure. As used herein, "controlled manner" means the time needed to form the bond can vary from 1 second to 48 hours.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A mitral valve replacement device adapted to be deployed at a mitral valve position in a human heart, comprising:
    an atrial flange defining an atrial end of the device, the atrial flange having a ventricular end that extends horizontally in a radial direction;
    a ventricular portion defining a ventricular end of the device;
    a neck positioned between the atrial flange and the ventricular portion;
    an annulus support that is positioned between the ventricular portion and the neck, the annulus support including a ring of anchors, each anchor extending radially from the neck and ending in a rounded tip that bends in a circumferential direction, each anchor further including a segment that extends radially outwardly from the tip, then bends longitudinally toward the ventricular end, and then bends radially inwardly, with an annular clipping space defined between the atrial flange and the ring of anchors;
    a plurality of leaflet holders positioned at the atrial end of the atrial flange; and
    a plurality of valve leaflets secured to the leaflet holders, and positioned inside the atrial flange at a location above the native annulus.

2. The device of claim 1, wherein at least a portion of one or more of the atrial flange, the annulus support and the ventricular portion is covered with tissue, fabric, or both tissue and fabric.

3. The device of claim 1, further including at least one tail extending from the ventricular end of the ventricular portion.

4. The device of claim 1, wherein at least a portion of one or more of the atrial flange, the annulus support and ventricular portion is coated with a biocompatible adhesive.

5. The device of claim 1, wherein the ventricular portion has a height ranging between 2 mm to 15 mm.

6. The device of claim 1, wherein the atrial flange includes a plurality of tabs arranged in an annular manner.

7. The device of claim 1, wherein the ventricular portion comprises a plurality of V-shaped tabs.

* * * * *